United States Patent
Bojarski et al.

(10) Patent No.: US 7,988,732 B2
(45) Date of Patent: *Aug. 2, 2011

(54) SHEATHS FOR IMPLANTABLE FIXATION DEVICES

(75) Inventors: Raymond C. Bojarski, Attleboro, MA (US); Paul Alexander Torrie, Marblehead, MA (US); Fraser Harvie, East Kilbride (GB); Steven W. Ek, Bolton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/776,506

(22) Filed: May 10, 2010

(65) Prior Publication Data
US 2010/0222826 A1    Sep. 2, 2010

Related U.S. Application Data

(63) Continuation of application No. 11/970,196, filed on Jan. 7, 2008, now Pat. No. 7,731,750.

(51) Int. Cl.
*A61F 2/08* (2006.01)
(52) U.S. Cl. .................................. 623/13.15
(58) Field of Classification Search ..... 623/13.11–13.19
See application file for complete search history.

(56) References Cited

U.S. PATENT DOCUMENTS

| | | | |
|---|---|---|---|
| 3,921,496 A | 11/1975 | Helderman | |
| 4,605,414 A | 8/1986 | Czajka | |
| 4,790,850 A | 12/1988 | Dunn et al. | |
| 5,071,420 A | 12/1991 | Paulos et al. | |
| 5,084,050 A | 1/1992 | Draenert | |
| 5,139,520 A | 8/1992 | Rosenberg | |
| 5,197,976 A | 3/1993 | Herweck et al. | |
| 5,380,334 A | 1/1995 | Torrie et al. | |
| 5,383,878 A | 1/1995 | Roger et al. | |
| 5,439,684 A | 8/1995 | Prewett et al. | |
| 5,456,274 A | 10/1995 | Selbee et al. | |
| 5,456,685 A | 10/1995 | Huebner | |
| 5,456,721 A | 10/1995 | Legrand | |
| 5,490,750 A | 2/1996 | Gundy | |
| 5,632,748 A | 5/1997 | Beck, Jr. et al. | |
| 5,641,256 A | 6/1997 | Gundy | |
| 5,671,695 A | 9/1997 | Schroeder | |
| 5,683,419 A | 11/1997 | Thal | |
| 5,713,904 A | 2/1998 | Errico et al. | |
| 5,716,359 A | 2/1998 | Ojima et al. | |

(Continued)

FOREIGN PATENT DOCUMENTS

DE    01107898    12/1989

(Continued)

OTHER PUBLICATIONS

Notification of Transmittal of the International Preliminary Report on Patentability mailed Jul. 27, 2005 for International Application No. PCT/US2004/003302 filed Feb. 4, 2004, 10 pages.

(Continued)

*Primary Examiner* — Suzette J Gherbi
(74) *Attorney, Agent, or Firm* — Norman F. Heiner, Jr.

(57) ABSTRACT

Sheaths for implantable fixation devices are disclosed. Sheaths have a flexible body with a perforated wall, an open end, a closed end, and a body interior sized and shaped to receive the fixation device.

23 Claims, 10 Drawing Sheets

U.S. PATENT DOCUMENTS

| | | | |
|---|---|---|---|
| 5,720,765 A | 2/1998 | Thal | |
| 5,769,894 A | 6/1998 | Ferragamo | |
| 5,899,938 A | 5/1999 | Sklar et al. | |
| 5,935,129 A | 8/1999 | McDevitt et al. | |
| 5,964,764 A | 10/1999 | West et al. | |
| 5,984,926 A | 11/1999 | Jones | |
| 6,143,029 A * | 11/2000 | Rippstein | 623/13.14 |
| 6,203,572 B1 | 3/2001 | Johnson | |
| 6,409,750 B1 | 6/2002 | Hyodoh et al. | |
| 6,454,808 B1 | 9/2002 | Masada | |
| 6,533,816 B2 | 3/2003 | Sklar | |
| 6,602,290 B2 | 8/2003 | Esnouf et al. | |
| 6,746,483 B1 * | 6/2004 | Bojarski et al. | 623/13.14 |
| 6,840,770 B2 | 1/2005 | McDevitt | |
| 7,220,283 B2 | 5/2007 | Terrill | |
| 7,279,008 B2 | 10/2007 | Brown et al. | |
| 7,407,512 B2 * | 8/2008 | Bojarski et al. | 623/13.14 |
| 7,731,750 B2 * | 6/2010 | Bojarski et al. | 623/13.15 |
| 2002/0055749 A1 | 5/2002 | Esnouf et al. | |
| 2002/0108622 A1 | 8/2002 | Whelan | |
| 2009/0202963 A1 | 8/2009 | McDevitt | |

FOREIGN PATENT DOCUMENTS

| | | |
|---|---|---|
| EP | 0280572 | 8/1988 |
| EP | 0556571 | 8/1993 |
| EP | 0893109 | 1/1999 |
| FR | 2714817 | 7/1995 |
| JP | 10014936 A | 1/1998 |
| WO | WO9639082 A1 | 12/1996 |
| WO | 9822047 | 5/1998 |
| WO | 9837835 | 9/1998 |
| WO | 9901084 | 1/1999 |
| WO | 0170135 | 9/2001 |

OTHER PUBLICATIONS

USPTO Non-final Office Action in U.S. Appl. No. 12/201,184, mailed May 6, 2009, 10 pages.

International Search Report for PCT/US01/08124, mailed Oct. 29, 2001.

Pinczewski et al., "Case Report—Integration of Hamstring Tendon Graft With Bone in Reconstruction of the Anterior Cruciate Ligament," Arthroscopy: The Journal of Arthroscopic and Related Surgery, vol. 13, No. 5, pp. 641-643 (Oct. 1997).

* cited by examiner

SHEATHS FOR IMPLANTABLE FIXATION DEVICES

CROSS-REFERENCE TO RELATED APPLICATIONS

This application is a continuation of U.S. application Ser. No. 11/970,196, filed Jan. 7, 2008, which is a divisional of U.S. application Ser. No. 10/862,573, filed Jun. 8, 2004, which is a continuation of U.S. application Ser. No. 09/526,960, filed Mar. 16, 2000, now U.S. Pat. No. 6,746,483, the disclosures of which are incorporated herein by reference in their entireties.

BACKGROUND OF THE INVENTION

The invention relates to devices that fix soft tissue to support structures, particularly devices that fix soft tissue grafts within bone tunnels.

In certain types of surgical procedures, soft tissue grafts must be fixed within a bone tunnel. For example, in anterior cruciate ligament (ACL) replacement surgery, a ligament graft is harvested from the patient or from a donor, and implanted within the knee by securing one end within a bone tunnel drilled through the tibia, and the other end within a bone tunnel drilled through the femur. Several ACL reconstructive techniques are described in Rosenberg, U.S. Pat. No. 5,139,520, which is incorporated herein by reference.

Referring to FIG. 1, a ligament graft 10 can be fixed within a bone tunnel using a bone screw 12. Graft 10 is made from e.g., a single or double long strip of soft tissue. To implant graft 10, the middle of the strip (not shown) is first passed in a distal direction through a first tunnel 14 in the tibia into a second tunnel 18 in the femur, and then attached to the femur tunnel (or attached to bone adjacent the femur tunnel) with a femur fixation device (not shown). Two approximately equal length segments 19a, 19b of the graft extend proximally from the attached middle portion through tunnels 18 and 14. The two ends 20a, 20b of segments 19a, 19b terminate proximal to tibial tunnel 14. Segments 19a and 19b of the graft are then fixed within tibial tunnel 14 by inserting bone screw 12 between the two segments, such that shaft 22 of the screw presses the segments against internal wall 24 of tunnel 14.

In attaching soft tissue within a bone tunnel using a bone screw, it is important that the tissue be rigidly fixed within the tunnel to prevent slippage. When the bone involved is relatively soft (less calcified), a common problem in elderly patients, screws may not adequately fix the graft to the bone.

SUMMARY OF THE INVENTION

In one aspect, the invention relates to a sheath for an implantable fixation device, the sheath comprising a flexible body having a relieved wall, the body defining an interior sized and shaped to receive the fixation device and including an open end and a closed end. In an embodiment, the body defines a tube, the tube being sized and shaped to receive the fixation device. In another embodiment, the tube is sized and shaped to snugly receive a shaft of a bone screw fixation device. In another embodiment, the relieved wall comprises a mesh wall. In yet another embodiment, the flexible body comprises a tube that defines at least one perforation in a circumferential side wall of the tube. In a further embodiment, the flexible body includes an interior that is flexible such that, when the fixation device is inserted into the body, the body flexibly expands to allow the fixation device to fit snugly within the body.

In another aspect, the invention relates to a combination comprising a sheath including a flexible body having a relieved wall, the body defining an interior sized and shaped to receive a fixation device and including an open end and a closed end; and the fixation device, wherein the fixation device is a bone screw, the bone screw having a shaft sized and shaped to fit within the interior of the sheath. In an embodiment, the shaft of the bone screw fits snugly within the interior of the sheath. In another embodiment, the shaft includes generally rounded screw threads. In yet another embodiment, the body defines a tube, the tube being sized and shaped to receive the fixation device. In a further embodiment, the relieved wall comprises a mesh wall. In yet a further embodiment, the flexible body comprises a tube that defines at least one perforation in a circumferential side wall of the tube. In an embodiment, the flexible body includes an interior that is flexible such that, when the fixation device is inserted into the body, the body flexibly expands to allow the fixation device to fit snugly within the body.

In yet another aspect, the invention relates to a combination comprising a sheath including a flexible body defining a tube having an open end and a closed end, the tube defining an interior sized and shaped to receive a fixation device and a soft tissue graft; and the fixation device, the fixation device configured to be received within the sheath such that the fixation device extends over a majority of the length of the tube. In an embodiment, the body includes a relieved wall. In another embodiment, the relieved wall comprises a mesh wall. In yet another embodiment, the tube defines at least one perforation in a circumferential side wall of the tube. In a further embodiment, the interior of the tube is flexible such that, when the fixation device and the soft tissue graft are inserted into the tube, the tube flexibly expands to allow the fixation device and the soft tissue graft to fit snugly within the tube.

In a further aspect, the invention relates to a sheath for an implantable fixation device, the sheath comprising a flexible body having a relieved wall, the body defining an interior sized and shaped to receive the fixation device and including an open and closed end, wherein the body defines a tube, the tube being sized and shaped to snugly receive a shaft of a bone screw fixation device.

In yet a further aspect, the invention relates to a sheath for an implantable fixation device, the sheath comprising a flexible body having a relieved wall, the body defining an interior sized and shaped to receive the fixation device, wherein the body defines a tube, the tube being sized and shaped to receive the fixation device and including an open end and a closed end.

In an aspect, the invention relates to a combination comprising a sheath including a flexible body having a relieved wall, the body defining an interior sized and shaped to receive a fixation device and an open end and a closed end; and the fixation device.

In another aspect, the invention relates to a combination comprising a sheath including: a flexible body having a relieved wall, the body defining an interior sized and shaped to receive a fixation device and including an open end and a closed end, and the fixation device, wherein the relieved wall comprises a mesh wall.

In yet another aspect, the invention relates to s sheath for an implantable fixation device, the sheath comprising a flexible body having a relieved wall, the body defining an interior sized and shaped to receive the fixation device and including an open end and a closed end, wherein the relieved wall comprises a mesh wall.

The invention may include one or more of the following advantages.

The flexibility and thinness of certain embodiments of the sheath allows the sheath to conform, e.g., to the shape of the fixation device, or to the shape of a bone tunnel.

In certain embodiments, the sheath protects the soft tissue graft from laceration or cutting by threads of a fixation screw, and reduces twisting of the graft upon insertion of a screw.

The relief in the sheath, e.g., perforations in a wall of the sheath, allows in situ contact between a soft tissue graft and the wall of a bone tunnel, promoting development of Sharpy-like fibers and permanent attachment of the soft tissue to the bone.

Therapeutic agents, such as osteoinductors or growth factors, can be disposed on or embedded into the material of the sheath, allowing delivery of the agent directly to the site of fixation.

Other embodiments and advantages of the invention will be apparent from the following description and from the claims.

DESCRIPTION OF THE PREFERRED EMBODIMENTS

Embodiments of the invention feature sheaths that surround bone screws and soft tissue grafts to improve fixation of the grafts. In its simplest form, the sheath is a flexible, mesh tube that surrounds only the bone screw, both the bone screw and the graft, or only the graft. In other embodiments, the sheath includes multiple tubes.

Figure 1:
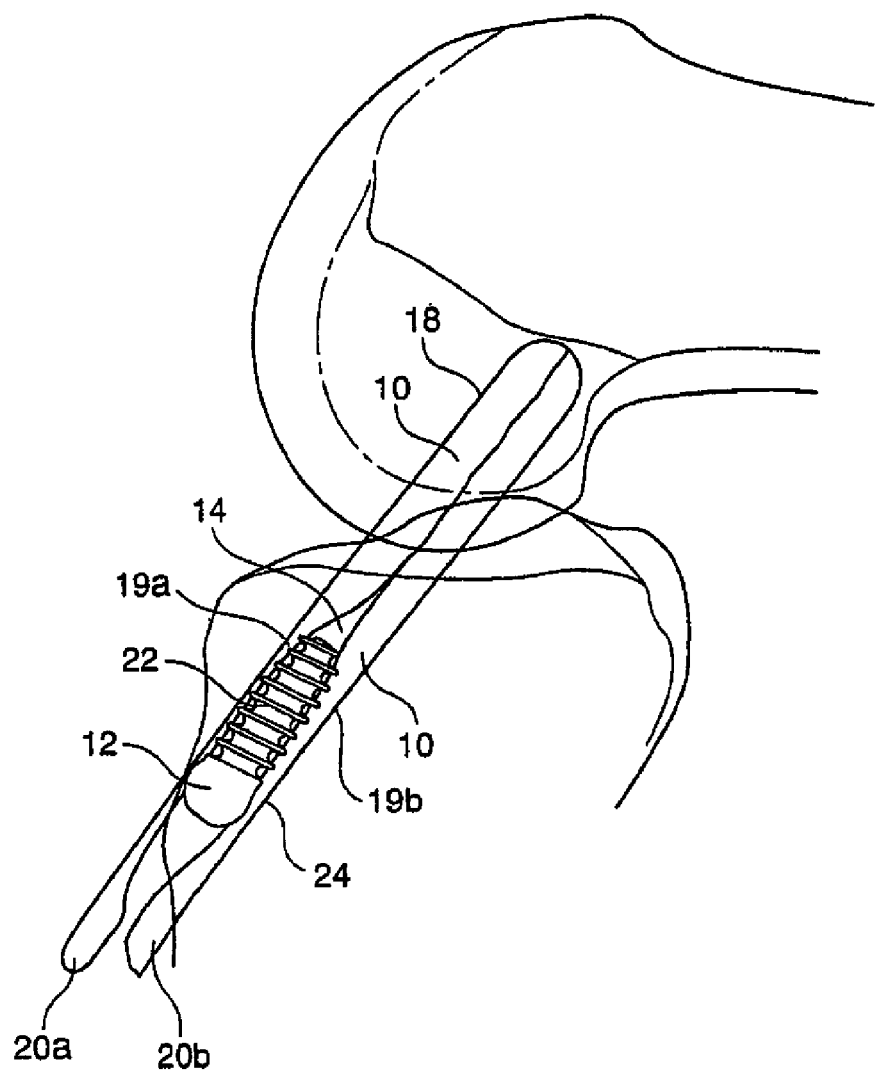
FIG. 1 is a sectional view of a prior art technique of fixing a ligament graft within a tibial bone tunnel by using a bone screw.
Figure 2A:
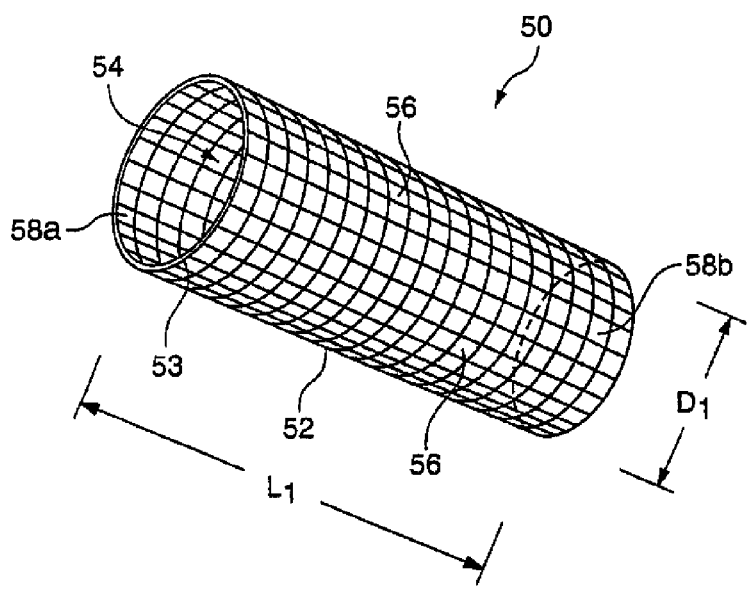
FIG. 2A is a perspective view of a bone screw sheath.
Figure 2B:
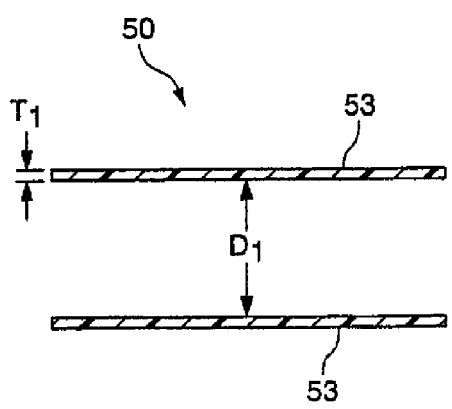
FIG. 2B is a sectional view of the bone screw sheath of FIG. 2A.
Figure 2C:
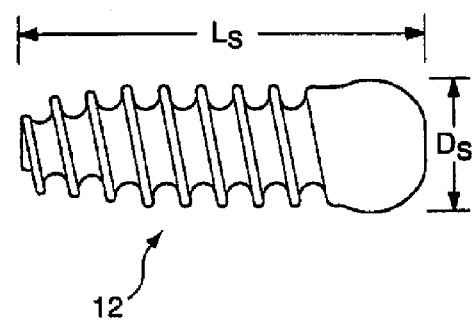
FIG. 2C is a sectional view of the bone screw of FIG. 1.

Referring to FIGS. 2A-2C, a sheath 50 has a tube-shaped body 52 that defines a generally cylindrical exterior surface 53 and a generally cylindrical interior 54. Body 52 is formed from a biocompatible material woven into a mesh structure. The mesh defines numerous holes 56 that expose interior 54 to the outside. Sheath 50 also has two circular, open ends 58a, 58b, allowing a tissue graft to pass entirely through the interior of the sheath.

Interior 54 of sheath 50 is sized and shaped to receive bone screw 12. Sheath 50 has an internal diameter $D_1$ greater than the diameter $D_S$ of bone screw 12, so that both screw 12 and segments 19a and 19b of graft 10 can fit snugly within the sheath. The sheath has a length $L_1$ slightly larger than the length $L_S$ of screw 12. The mesh body 52 is thin and flexible, allowing the sheath to adjust to snugly surround the screw; body 52 can be compressed to reduce the volume of interior 54, twisted, or stretched. Since sheath 50 is thin and flexible rather than rigid, it cannot on its own shore up soft bone, or fix a graft within a bone tunnel. (i.e., sheath 50 is not designed to be used alone as a fixation device or as a solid, rigid reinforcement of soft bone.)

In some embodiments, the threads forming the mesh body 52 are larger in the radial direction than in the axial direction. This difference in thread size results in sheath 50 being less flexible radially than axially. In these embodiments, the diameter $D_1$ is more resistant to expansion or contraction than length $L_1$. In other embodiments, the thread size is equal throughout body 52.

Diameter $D_1$ is, e.g., between about 8 and 10 mm, and $L_1$ is, between about 25 and 40 mm. If sheath 50 is designed for a 7×25 bone screw (7 mm diameter, 25 mm length), then $L_1$ is, e.g., about 30 mm, and $D_1$ is, e.g., about 9 mm. Most of exterior surface 53 is open. For example, about 40% of the area exterior surface 53 is mesh strands, and about 60% is holes 56. The thickness $T_1$ the mesh wall of sheath 50 is, for example, less than about 0.3 mm, e.g., about 0.1-0.2 mm.

Body 52 can be made from a variety of bioabsorbable materials, including polylactic acid, or polylactic glycolic acid. Alternatively, body 52 can be made from a blend of absorbable materials, or from a non-absorbable material, such as a polyester. The material forming the body preferably has a higher coefficient of friction than graft 10, so that exterior surface 53 of the sheath grips internal wall 24 of bone tunnel 14 more firmly than graft 10 alone, improving fixation.

Body 52 can be formed, e.g., by weaving, braiding, knitting, or crocheting strands of the material to form the cylindrical shape, or by extrusion, using techniques known in the art. The strands forming body 52 have diameters of about 0.1-1.0 mm, e.g., 0.4-0.6 mm, or 0.51 mm.

Although sheath 50 can be used with a variety of fixation screws, screw 12 preferably has blunt or rounded screw threads, as opposed to sharp threads, so that the threads do not cut the sheath or the soft tissue graft. A typical rounded-thread screw is shown in Roger et al., U.S. Pat. No. 5,383,878, which is incorporated herein by reference.

Figure 3:
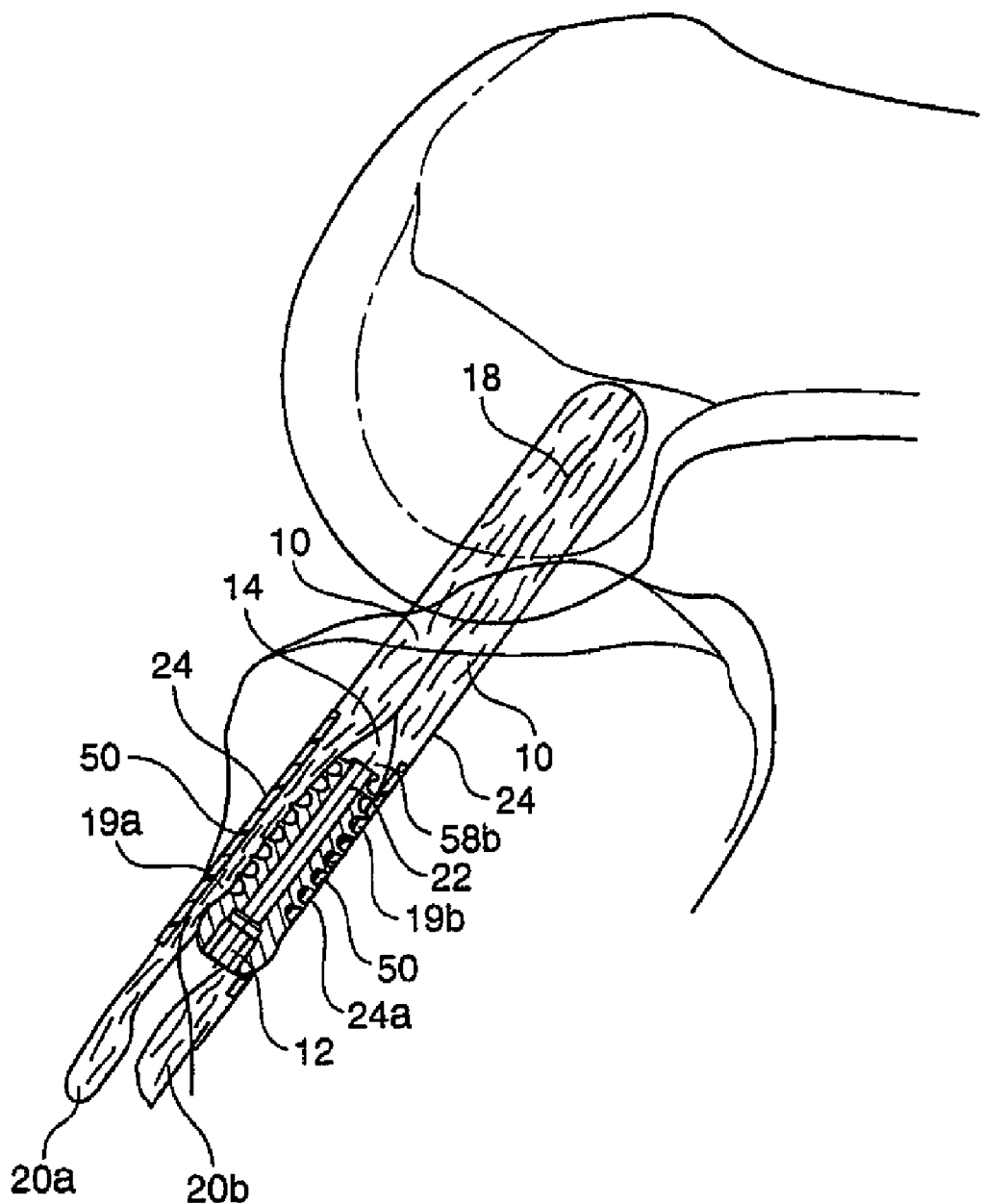
FIG. 3 is a sectional view of a the bone screw and sheath of FIGS. 2A-2C fixing a ligament graft within a bone tunnel in the tibia.

Referring to FIG. 3, in operation, a surgeon first forms bone tunnels 14 and 18 within the tibia and femur, respectively. Next, graft 10 is fixed to the femur tunnel using any technique known in the art (not shown). For example, the femur fixation device can include a loop attached to the femur at a distal end of femur tunnel 18. End 20a of the graft is passed distally through tunnels 14 and 18, passed through the loop, and then pulled proximally through tunnels 18 and 14 until the middle portion of the graft is centered on the loop. Alternatively, the graft can be threaded through the loop prior to implantation of the loop. In addition, rather than using a loop, one end of graft 10 can be fixed within the femur tunnel, allowing the other end to extend proximally through tunnels 18 and 14. To increase the number of segments available for fixation, multiple strips of soft tissue (i.e., multiple grafts) can be separately attached to the femur. Various techniques for attaching a graft within a bone tunnel are described in Ferragamo, U.S. Pat. No. 5,769,894, which is incorporated herein by reference, and in Rosenberg, supra.

After attaching graft 10 within (or adjacent to) femur tunnel 18, the surgeon passes ends 20a, 20b of graft 10 through interior 54 of sheath 50 (via open ends 58a and 58b), and then slides sheath 50 into tibial tunnel 14. The diameter of tunnel 14 is only slightly larger than the outer diameter of sheath 50, such that sheath 50 fits snugly within tunnel 14. Alternatively, sheath 50 can be inserted into tunnel 14 prior to passing the graft through the sheath. To insert sheath 50 into tibial tunnel 14, the surgeon can use a delivery tool, such as a rigid tube detachably fixed to the distal end of the sheath. Alternatively, a suture can be threaded through the distal end of sheath 50, and the sheath can be pulled into place within tunnel 14 using the suture.

The surgeon then inserts bone screw 12 into interior 54 of sheath 50, between segments 19a and 19b of the graft. The screw may be inserted using an insertion tool known in the art, such as a screw driver. When screw 12 is in place as shown in FIG. 3, the screw presses segments 19a and 19b of the graft against the interior surface of sheath 50, and presses exterior surface 53 of the sheath against wall 24, fixing the graft within the tunnel.

As shown in FIG. 3, when screw 12 is inserted, it will typically be slightly off center, such that the screw's threads dig into wall 24 of bone tunnel 14 along a segment 24a of wall 24. For example, if screw 12 has a major diameter of 9 mm, and a minor diameter of 7 mm, then the screw threads will dig into wall 24 by about 1 mm along segment 24a, where segment 24a is about 120 degrees. This engagement of the threads with segment 24a of the wall helps hold screw 12 within tunnel 14, and therefore improves fixation of graft 10 within the tunnel.

The presence of sheath 50 within bone tunnel 14 improves fixation of graft 10. Since exterior surface 53 of sheath 50 has a higher coefficient of friction than graft 10, sheath 50 is less likely than graft 10 (which is made of tissue) to slide along wall 24 of the tunnel, or to twist when screw 12 is inserted into the tunnel. In addition, since body 52 of sheath 50 has a mesh structure, portions of graft 10 protrude through holes 56 of the mesh, resisting sliding of graft 10 relative to sheath 50. The flexibility of sheath 50 allows the sheath to conform to the shape of wall 24, maximizing the surface area contact between the exterior surface of the sheath and wall 24, thereby increasing frictional forces between the sheath and the wall.

After screw 12 has been inserted into tunnel 14, the surgeon may trim the portions of segments 19a and 19b that extrude proximally from tunnel 14, completing the surgical procedure. Over time, graft 10 permanently affixes to wall 24 by growth of Sharpy-like fibers between the soft tissue of graft 10 and the bone tissue of wall 24. ("Sharpy-like fibers" are collagenous fibers that grow from bone into a soft tissue graft. The presence of Sharpy-like fibers indicate good bony growth to the graft, and therefore good fixation. See Pinczewski et al., "Integration of Hamstring Tendon Graft With Bone in Reconstruction of the Anterior Cruciate Ligament," *Arthroscopy,* 13: 641-43 (1997). The open holes 56 in body 52 of the sheath facilitate permanent fixation by increasing the direct contact between the graft and the bone tunnel wall. Sheath 50 eventually dissolves, and new bone grows to fill its position.

To accelerate bone growth and permanent attachment of graft 10 to wall 24, sheath 50 can include an osteoinductive agent, such as hydroxyapatite, tricalcium phosphate, calcium sulphate, or a "ceramic" (a calcium and potassium crystalline). The osteoinductive agent can be applied to sheath 50 prior to surgery by, e.g., spraying the sheath with the agent, by dipping the sheath into a bath that includes the agent, by dusting or spraying the agent onto the sheath, or by filling the sheath with a gel that includes the agent. In addition, the strands of material forming the mesh body 52 can be hollow, and the agent can be within the hollow interiors of the strands. Alternatively, the agent can be incorporated into the material that forms body 52. For example, the agent can be blended into the material used to make the threads that form mesh body 52, or can be added to the fibers as an osteoinductive felt.

Other therapeutic agent, such as growth factors (e.g., tissue growth fact or platelet derived growth factor), bone morphogenic proteins, stem cells, osteoblasts, and cytokines, can also be included in the sheath. These bioactive agents can be added using the techniques described above, or can be blended into the material that forms body 52 using micro-encapsulation or nanoparticles. For example, body 52 can be formed from a material comprising microspheres of the agent and a polymer, such as polylactic glycolic acid. The microspheres of the agent and polymer can be prepared using known techniques. See, e.g., Cohen et al., "Controlled Delivery Systems for Proteins Based on Poly(Lactic/Glycolic Acid) Microspheres," *Pharm. Research,* 8:713-20 (1991); DeLuca et al., U.S. Pat. Nos. 5,160,745 and 4,741,872. Rather than forming microspheres, the agent and polymer can also be mixed together using, e.g., sintering techniques. See, Cohen et al., "Sintering Techniques for the Preparation of Polymer Matrices for the Controlled Release of Macromolecules," *J. Pharm. Sciences,* 73:1034-37 (1984). The bioactive agents can also be attached to body 52 using adhesives or electrical charge, or can be directly loaded onto the sheath by a delivery mechanism after implantation of the sheath.

Other embodiments are within the scope of the claims. For example, the sheath can be used to assist fixation of a bone screw within the femur tunnel 18, in addition to the tibial tunnel 14.

Figure 4:
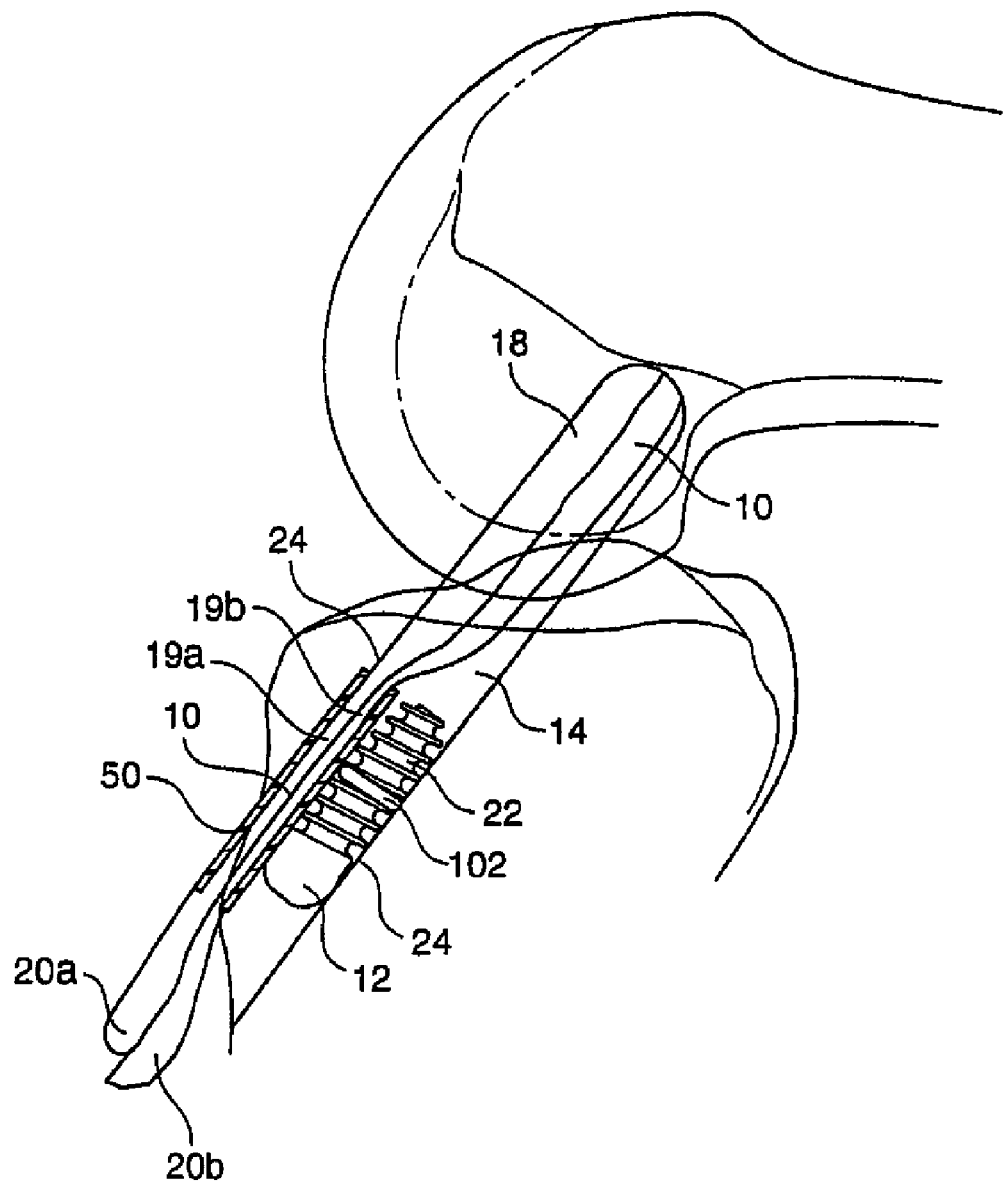
FIGS. 4 and 5 are sectional views illustrating alternative arrangements for the bone screw, sheath, and graft of FIG. 3 within the bone tunnel in the tibia.

Referring to FIG. 4, screw 12 can be placed between sheath 50 and wall 24 of tunnel 14. In this embodiment, rather than inserting screw 12 into the sheath after placement of the sheath within tunnel 14, screw 12 is inserted into tunnel 14 along the side of the sheath. To hold screw 12 to the side of the sheath, the sheath can optionally include an external loop 102. Loop 102 has a diameter slightly larger than the diameter of screw 12, so that shaft 22 of screw 12 fits snugly within the loop. Loop 102 can be made from the same material as body 52, or can be made from an inflexible, rigid material.

When screw 12 is inserted, it compresses graft 10 within the sheath, and presses exterior surface 53 of the sheath against wall 24, fixing graft 10 within tunnel 14.

Figure 5:
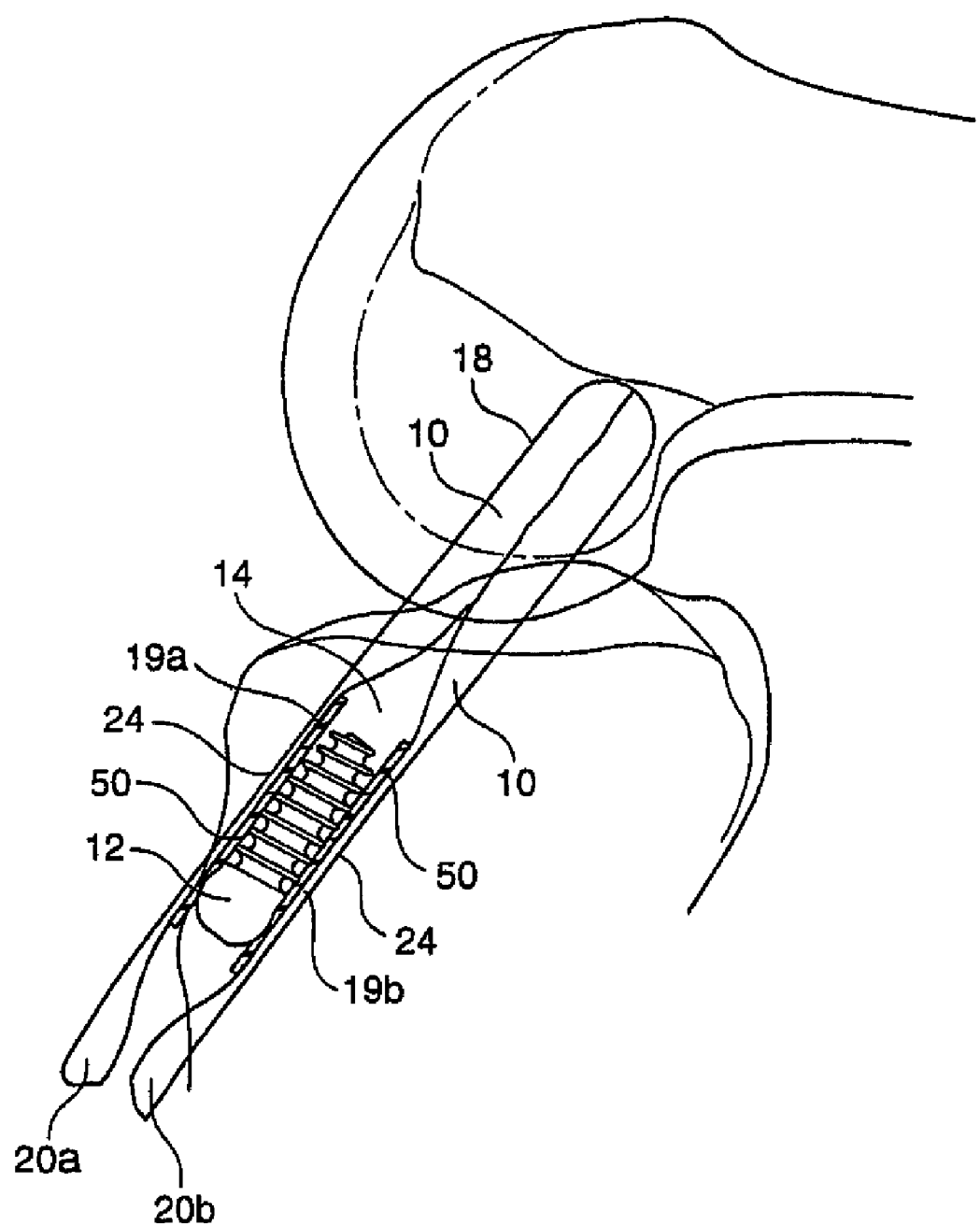

Referring to FIG. 5, segments 19a and 19b of graft 10 can be positioned radially outside of sheath 50. In this embodiment, when sheath 50 is inserted into tunnel 14, it is located between ends 19a and 19b of the graft, so that the graft surrounds the sheath, rather than the sheath surrounding the graft. Screw 12 is then inserted into the sheath, pressing segments 19a and 19b between exterior surface 53 of the sheath and wall 24, fixing the graph in place. Alternatively, the screw can first be inserted into the sheath, and then the sheath and screw together can be positioned within the bone tunnel.

The structure of the bone screw sheath can be modified as well. The diameter D1, length L1, and thickness T of the sheath can be varied to accommodate different sized bone tunnels, different sized screws, and different deployment methods. For example, in the deployment method of FIG. 5, the inner diameter D1 of the sheath can be approximately equal to the diameter DS of the screw shaft, so that the screw fits very snugly within the sheath, and exterior surface 53 of the sheath conforms to the shape of the screw shaft.

In the deployment methods shown in FIGS. 4 and 5, the sheath need not be more rigid in the radial direction than in the axial direction. The threads forming the mesh body, therefore, are generally the same size in both the radial and axial directions. In addition, sheaths used in the deployment method of FIG. 5 can have less open space than sheaths used with the method of FIG. 3 or 4. (i.e., less than 60% of the sheath's surface area will be holes.)

If the bone is particularly soft, sheath 50 can be woven tighter, so that the sheath is less flexible, thereby providing a more firm substrate for screw 12 to engage.

The sheath need not have a mesh structure. For example, the sheath can have a solid body with holes cut through the body, allowing communication between the exterior and interior of the sheath. In addition, the sheath's body need not be integrally formed. For example, the body can be formed by winding a strip of material around an implantable device to form a relieved body that defines an interior.

The sheath can have relief structures other than holes to allow communication between the exterior and interior. For example, other types of perforations, such as slits, can be used, instead of holes. In addition, the device can have a solid wall with thinned sections. When implanted, the thinned sections biodegrade more quickly than other sections of the wall, such that in situ, the device develops perforations.

Figure 6:
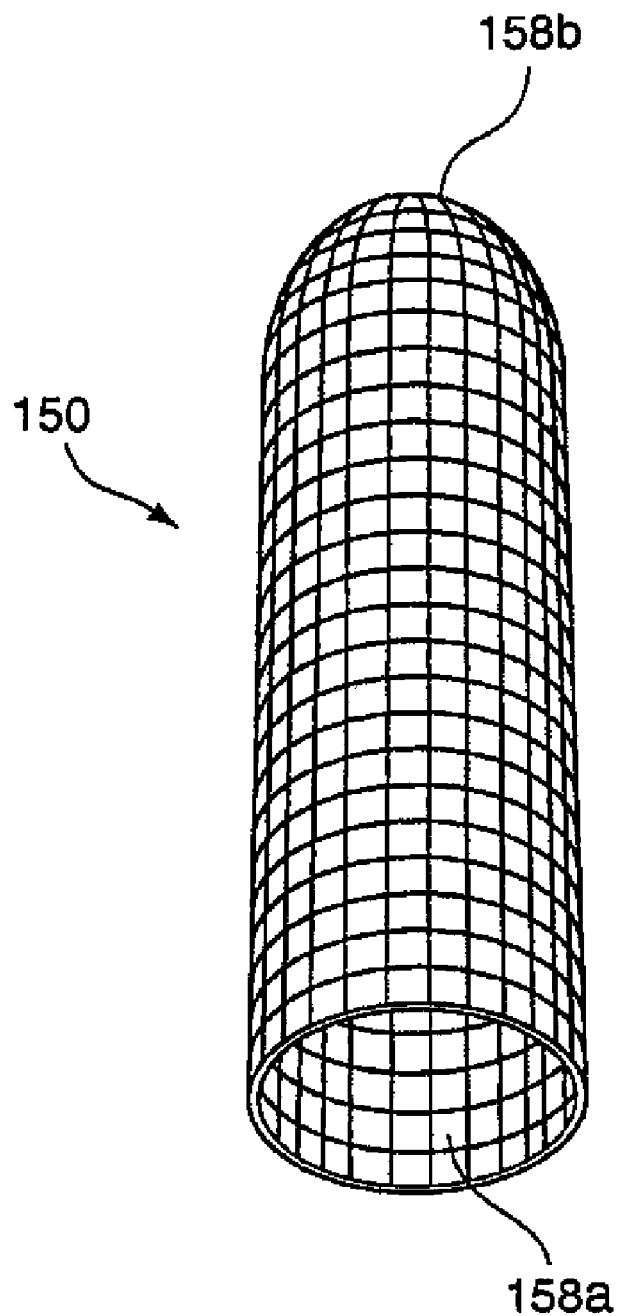
FIG. 6 is a perspective view of an alternative embodiment of the sheath of FIG. 2A.

To increase the coefficient of friction of exterior surface 53 to improve fixation of the sheath within the bone tunnel, exterior surface 53 can have a roughened finish. Referring to FIG. 6, rather than having two open circular ends, sheath 150 has an open end 158a and a closed end 158b. Closed end 158b gives sheath a "bag" or "sock" shaped structure.

Figure 7A:
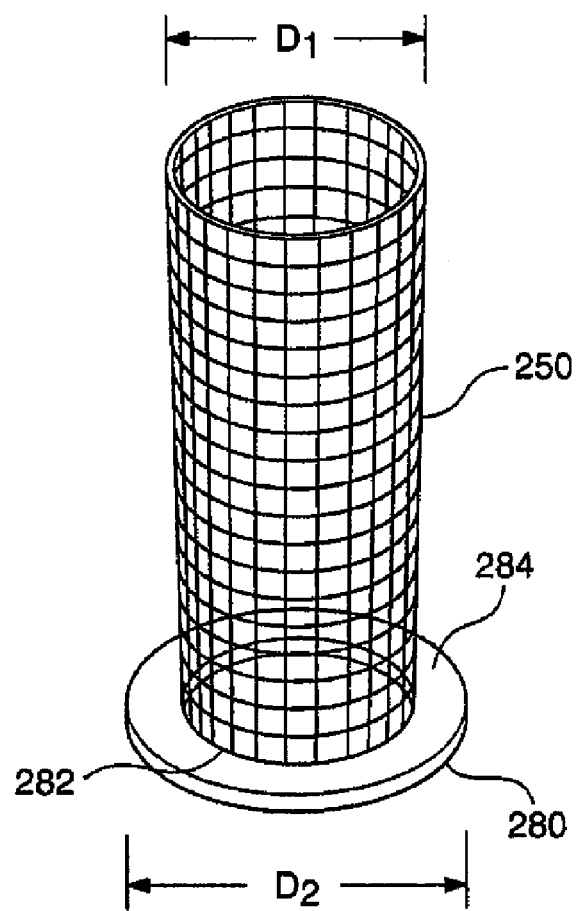
FIG. 7A is a perspective view of an alternative embodiment of the sheath of FIG. 2A that includes a washer.
Figure 7B:
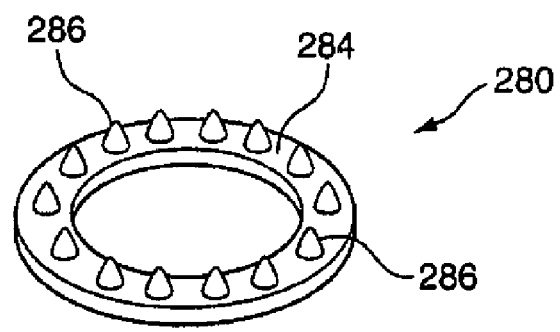
FIG. 7B is a top view of the washer of FIG. 7A.

Referring to FIG. 7A, a sheath 250 includes a washer 280 attached to the proximal end 282 of the sheath. The washer 280 has a diameter D2 that is larger than diameter D1 of sheath 250, and is larger than the diameter of the bone tunnel. Washer 280 prevents proximal end 282 of the sheath from passing into the bone tunnel when the screw is inserted into the sheath, thereby ensuring that the sheath is ultimately positioned around the screw shaft, rather than in front of the screw. Rather than being circular, the washer can be square, triangular, or any other shape, so long as it has a dimension larger than the diameter of the bone tunnel. Referring to FIG. 7B, the upper surface 284 of the washer can include teeth or spikes 286 to grip bone, thereby reducing twisting of sheath 250 when a bone screw is inserted into the sheath. The washer can be made from a bioabsorbable material, or a non-absorbable, biocompatible material. In operation, the washer can be detached from the sheath after implantation of the graft and bone screw, or can be left attached to the sheath.

Figure 8:
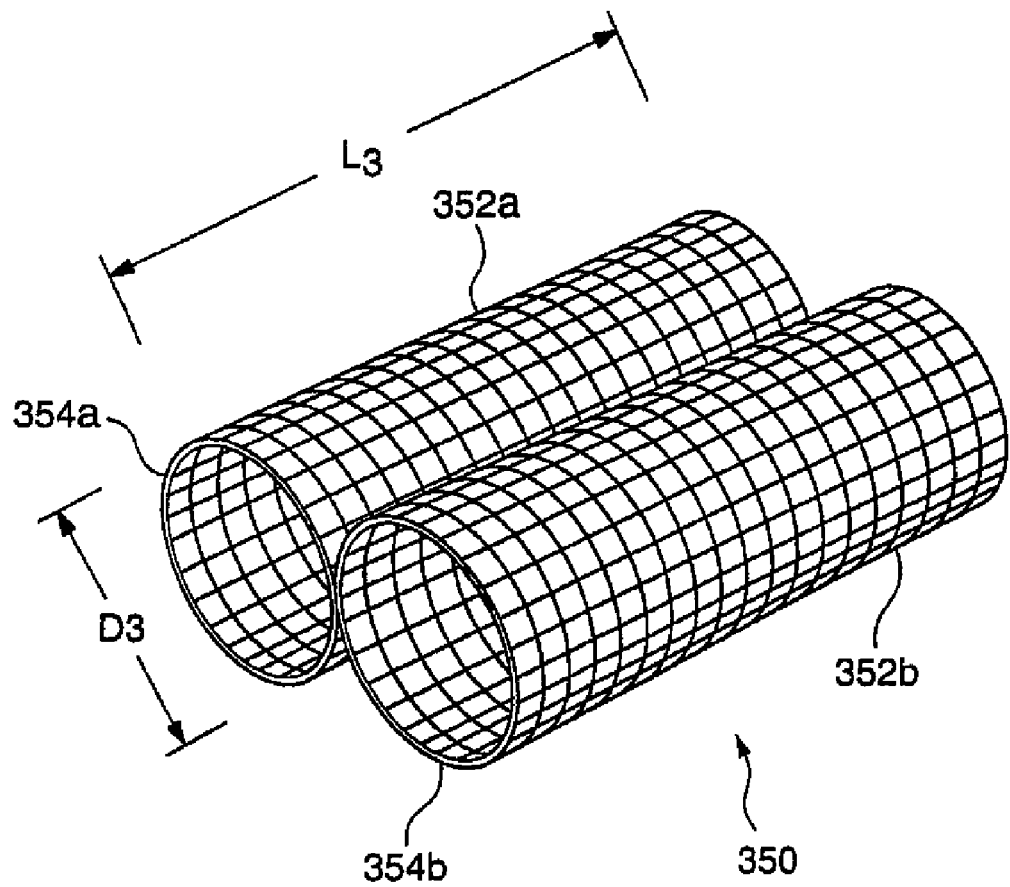
FIG. 8 is a perspective view of an alternative bone screw sheath that includes two tubes.

Referring to FIG. 8, a sheath 350 includes two contiguous, parallel mesh tubes, 352a and 352b. Tubes 352a and 352b are integrally woven, braided, knitted, or crocheted from threads. Each tube has a diameter D3 that is slightly larger than diameter DS of screw 12, and slightly less than diameter D1 of sheath 50. Diameter D3 can be, e.g., 2 mm, 4 mm, 6 mm, or 8 mm. Sheath 50 has a length L3 approximately equal to the length of a fixation screw, e.g., about 10-50 mm, or 20-35 mm. The walls 354a, 354b of tubes 352a and 352b each have a thickness of, e.g., between 0.1 mm and 1.0 mm.

In operation, a soft tissue graft is passed through one of the tubes (e.g., tube 352a), and the fixation screw is inserted into the second tube (e.g., tube 352b). When the sheath, graft, and fixation screw are positioned within the bone tunnel, tube 352a is compressed between the screw and a wall of the bone tunnel. The graft, therefore, is compressed within tube 352a, fixing the graft within the bone tunnel.

Figure 9:
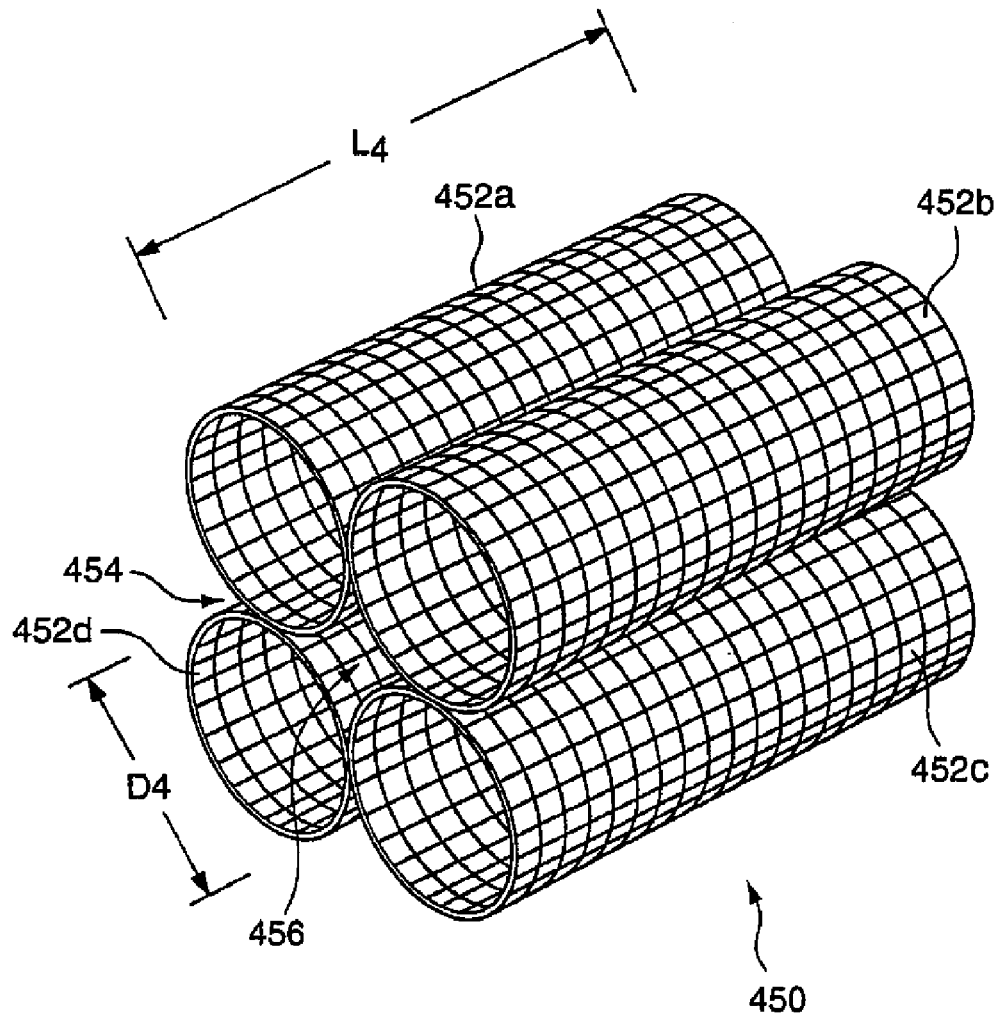
FIG. 9 is a perspective view of an alternative bone screw sheath that includes four tubes arranged to form a ring.

Referring to FIG. 9, a sheath 450 includes four parallel mesh tubes, 452a, 452b, 452c, and 452d. The four tubes are arranged to form a ring 454. Ring 454 defines a central cavity 456 disposed between the tubes. The cavity defines an axial bore that is coextensive with the axial lengths of each of the tubes.

Each tube 452a, 452b, 452c, and 452d has a diameter D4 and a length L4 similar to diameter D3 and length L3 of sheath 350 (FIG. 8). As with sheath 350, the tubes of sheath 450 are integrally woven.

In operation, segments of a soft tissue graft are passed through each of tubes 452a-452d. The surgeon can either use multiple, independent tissue grafts separately attached to the femur tunnel, or can split the proximal end of a single graft into four separate segments. The sheath is then inserted into the tibial bone tunnel, and a fixation screw is inserted into central cavity 456. When the sheath, soft tissue, and screw are in place within the bone tunnel, the tubes are compressed between the screw and the bone tunnel wall, and the soft tissue segments are compressed within each tube, thereby fixing the soft tissue within the bone tunnel.

In the embodiment shown FIG. 9, sheath 450 includes four tubes forming a ring. The sheath need not, however, be limited to this number. For example, the sheath can include a ring of 3, 5, 6, 7, or 8 tubes. In addition, soft tissue need not be passed through each tube. For example, soft tissue segments can be passed through two tubes, leaving the remaining tubes unoccupied.

Instead of being integrally woven, the tubes of sheath 450 can be woven, braided, or knitted separately, and attached together using, e.g., stitching, spot welding, or an adhesive. The tubes can also be solid rather than mesh, and need not all have the same diameter. In addition, unlike the single tube sheaths of FIGS. 2A, 6, and 7, sheath 450 can be rigid, rather than flexible.

Figure 10:
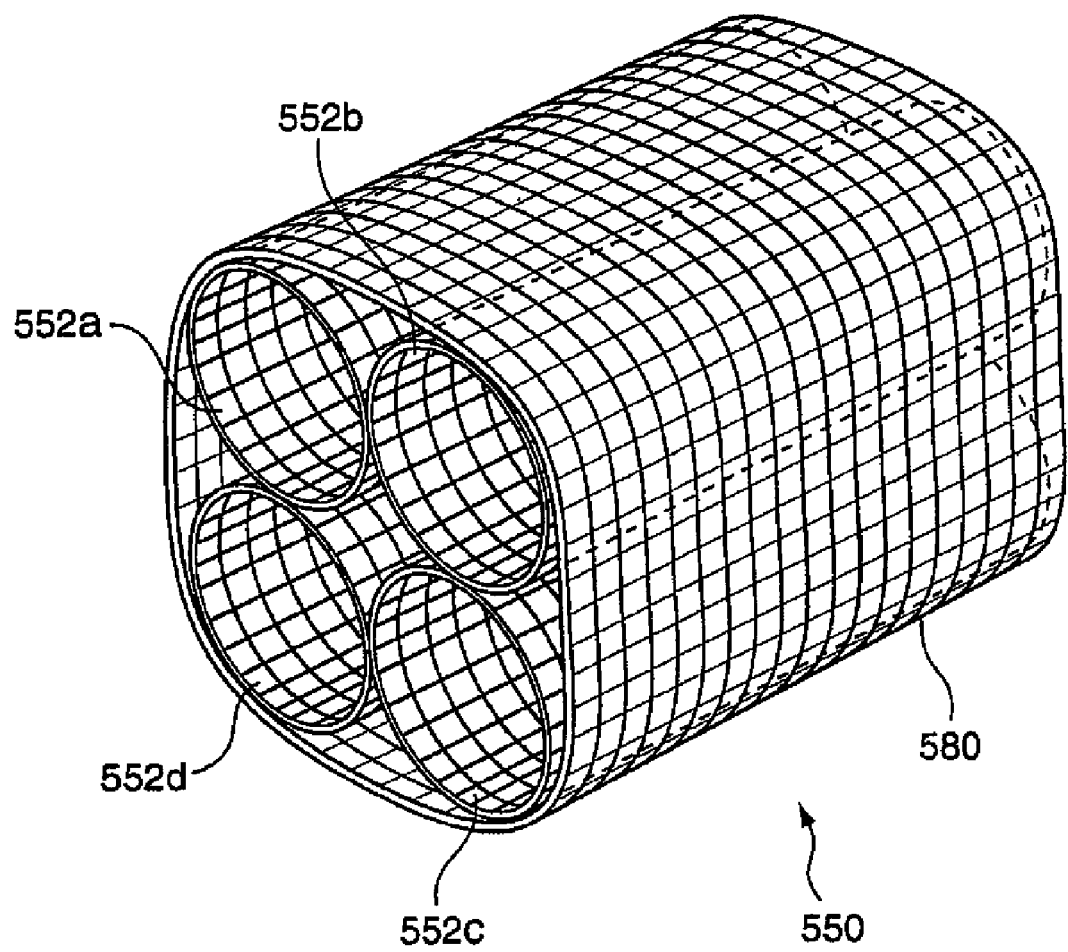
FIG. 10 is a perspective view of the bone screw sheath of FIG. 9 with an external sleeve.

Referring to FIG. 10, sheath 550 is identical to sheath 450 in all respects, except that sheath 550 further includes a mesh sleeve 580 that surrounds the four tubes 552a-552d. Sleeve 580 is axially coextensive with tubes 552a-552d, and is integrally woven with the four tubes. Alternatively, sleeve 580 can be a separate solid or mesh structure adhesively bound to the four tubes. Sleeve 580 acts to stabilize sheath 550, and facilitates insertion of the sheath into the bone tunnel. For example, to insert sheath 550, a suture or delivery tool can be attached to sleeve 580, rather than directly to one of the tubes.

The sheaths need not be used exclusively with bone screws or bone tunnels. Rather, the invention includes sheaths that improve fixation of other types of implantable fixation devices, such as soft tissue tacks, plugs, and suture anchors. The size and shapes of the sheaths can be varied to accommodate the different types of fixation devices. For example, in one embodiment, soft tissue can be positioned inside of a sheath, and the sheath can be attached to the side of a bone with a fixation device such as a tack.

What is claimed is:

1. A combination of a sheath and an implantable fixation device, the combination comprising:
   the sheath, the sheath comprising a flexible body having a relieved wall, the body defining an interior sized and shaped to receive the fixation device and including an open end and a closed end; and
   the fixation device, wherein the fixation device is a bone screw.

2. The combination sheath of claim 1, wherein the body defines a tube, the tube being sized and shaped to receive the fixation device.

3. The combination sheath of claim 2, wherein the tube is sized and shaped to snugly receive a shaft of a the bone screw fixation device.

4. A combination comprising:
a sheath including:
- a flexible body having a relieved wall, the body defining an interior sized and shaped to receive a fixation device and including an open end and a closed end; and
- the fixation device, wherein the fixation device is a bone screw, the bone screw having a shaft sized and shaped to fit within the interior of the sheath.

5. The combination of claim 4, wherein the shaft of the bone screw fits snugly within the interior of the sheath.

6. The combination of claim 4, wherein the shaft includes generally rounded screw threads.

7. The combination of claim 4, wherein the body defines a tube, the tube being sized and shaped to receive the fixation device.

8. A combination comprising:
a sheath including:
- a flexible body defining a tube having an open end and a closed end, the tube defining an interior sized and shaped to receive a fixation device and a soft tissue graft; and
- the fixation device, the fixation device configured to be received within the sheath such that the fixation device extends over a majority of the length of the tube wherein the fixation device is a bone screw.

9. The combination of claim 1, wherein the relieved wall comprises a mesh wall.

10. The combination of claim 1, wherein the flexible body comprises a tube that defines at least one perforation in a circumferential side wall of the tube.

11. The combination of claim 1, wherein the flexible body includes an interior that is flexible such that, when the fixation device is inserted into the body, the body flexibly expands to allow the fixation device to fit snugly within the body.

12. The combination of claim 4, wherein the relieved wall comprises a mesh wall.

13. The combination of claim 4, wherein the flexible body comprises a tube that defines at least one perforation in a circumferential side wall of the tube.

14. The combination of claim 4, wherein the flexible body includes an interior that is flexible such that, when the fixation device is inserted into the body, the body flexibly expands to allow the fixation device to fit snugly within the body.

15. The combination of claim 8, wherein the body includes a relieved wall.

16. The combination of claim 15, wherein the relieved wall comprises a mesh wall.

17. The combination of claim 8, wherein the tube defines at least one perforation in a circumferential side wall of the tube.

18. The combination of claim 8, wherein the interior of the tube is flexible such that, when the fixation device and the soft tissue graft are inserted into the tube, the tube flexibly expands to allow the fixation device and the soft tissue graft to fit snugly within the tube.

19. A combination of a sheath and an implantable fixation device, the combination comprising:
- the sheath comprising a flexible body having a relieved wall, the body defining an interior sized and shaped to receive the fixation device and including an open and closed end, wherein the body defines a tube, the tube being sized and shaped to snugly receive a shaft of a bone screw fixation device; and
- the bone screw fixation device.

20. A combination of a sheath and an implantable fixation device, the combination comprising:
- the sheath comprising a flexible body having a relieved wall, the body defining an interior sized and shaped to receive the fixation device, wherein the body defines a tube, the tube being sized and shaped to receive the fixation device and including an open end and a closed end; and
- the fixation device, the fixation device comprising a bone screw.

21. A combination comprising:
a sheath including:
- a flexible body having a relieved wall, the body defining an interior sized and shaped to receive a fixation device and an open end and a closed end; and
- the fixation device, the fixation device comprising a bone screw.

22. A combination comprising:
a sheath including:
- a flexible body having a relieved wall, the body defining an interior sized and shaped to receive a fixation device and including an open end and a closed end, and
- the fixation device comprising a bone screw, wherein the relieved wall comprises a mesh wall.

23. A combination of a sheath and an implantable fixation device, the combination comprising:
- the sheath, the sheath comprising a flexible body having a relieved wall, the body defining an interior sized and shaped to receive the fixation device and including an open end and a closed end, wherein the relieved wall comprises a mesh wall: and the fixation device, the fixation device comprising a bone screw.

* * * * *